(12) United States Patent
Lemanski et al.

(10) Patent No.: US 7,425,647 B2
(45) Date of Patent: Sep. 16, 2008

(54) PROCESS FOR PREPARING A GROUP VIII-METAL CONTAINING CATALYST, USE THEREOF FOR PREPARING AN ALKENYL CARBOXYLATE

(75) Inventors: Michael Francis Lemanski, Houston, TX (US); John Robert Lockemeyer, Sugar Land, TX (US)

(73) Assignee: Shell Oil Company, Houston, TX (US)

( * ) Notice: Subject to any disclaimer, the term of this patent is extended or adjusted under 35 U.S.C. 154(b) by 257 days.

(21) Appl. No.: 10/473,516

(22) PCT Filed: Mar. 28, 2002

(86) PCT No.: PCT/US02/09632

§ 371 (c)(1),
(2), (4) Date: Sep. 29, 2003

(87) PCT Pub. No.: WO02/078843

PCT Pub. Date: Oct. 10, 2002

(65) Prior Publication Data

US 2004/0133034 A1    Jul. 8, 2004

(51) Int. Cl.
*C07C 67/05* (2006.01)
*B01J 23/00* (2006.01)
*B01J 21/00* (2006.01)
*B01J 20/00* (2006.01)

(52) U.S. Cl. .............. 560/241.1; 502/326; 502/330; 502/331; 502/333; 502/334; 502/335; 502/336; 502/337; 502/338; 502/339; 502/407; 502/439; 502/245; 502/258; 502/259; 502/260; 502/261; 502/262

(58) Field of Classification Search .......... 502/326, 502/330, 331, 333–339, 407, 439, 245, 258–262; 560/241.1
See application file for complete search history.

(56) References Cited

U.S. PATENT DOCUMENTS

| | | | |
|---|---|---|---|
| 2,386,499 A * | 10/1945 | Owen | 502/320 |
| 3,328,316 A * | 6/1967 | Mulaskey | 502/66 |
| 3,514,492 A * | 5/1970 | Page | 568/799 |
| 3,573,228 A * | 3/1971 | Holmes et al. | 502/11 |
| 3,743,607 A | 7/1973 | Sennewald et al. | |
| 3,822,308 A | 7/1974 | Kronig et al. | |
| 4,048,096 A | 9/1977 | Bissot | |
| 4,497,908 A * | 2/1985 | Lewis et al. | 502/245 |
| 5,179,056 A | 1/1993 | Bartley | 502/170 |
| 5,179,057 A | 1/1993 | Bartley | |
| 5,185,308 A | 2/1993 | Bartley et al. | |
| 5,189,004 A | 2/1993 | Bartley | |
| 5,225,388 A | 7/1993 | Wunder et al. | |
| 5,250,487 A | 10/1993 | Wirtz et al. | |
| 5,274,181 A | 12/1993 | Bartley | |
| 5,292,931 A | 3/1994 | Wirtz et al. | |
| 5,314,858 A | 5/1994 | Colling | |
| 5,332,710 A * | 7/1994 | Nicolau et al. | 502/243 |
| 5,342,987 A | 8/1994 | Bartley | |
| 5,364,826 A * | 11/1994 | Kemp | 502/315 |
| 5,422,329 A | 6/1995 | Wirtz et al. | |
| 5,466,652 A * | 11/1995 | Paparizos et al. | 502/330 |
| 5,559,071 A | 9/1996 | Abel et al. | |
| 5,571,771 A | 11/1996 | Abel et al. | |
| 5,674,800 A | 10/1997 | Abel et al. | |
| 5,691,267 A * | 11/1997 | Nicolau et al. | 502/330 |
| 5,777,156 A | 7/1998 | Abel et al. | |
| 5,783,726 A * | 7/1998 | Lemanski et al. | 560/261 |
| 5,854,171 A * | 12/1998 | Nicolau et al. | 502/330 |
| 5,968,860 A | 10/1999 | Herzog | |
| 5,972,824 A | 10/1999 | Herzog et al. | |
| 6,022,823 A | 2/2000 | Augustine et al. | |
| 6,034,030 A * | 3/2000 | Nicolau et al. | 502/326 |
| 6,107,513 A | 8/2000 | Herzog et al. | |
| 6,114,571 A | 9/2000 | Abel et al. | |
| 6,114,573 A | 9/2000 | Herzog | |
| 6,143,921 A | 11/2000 | Karim et al. | 560/245 |

(Continued)

FOREIGN PATENT DOCUMENTS

CA    2018991    12/1990

(Continued)

OTHER PUBLICATIONS

S. Brunauer, P.Y. Emmett and E. Teller, J., "Adsorption of Gases in Multimolecular Layers", Am. Chem. Soc. vol. 60, 309-316, publ. Feb. 1938.

(Continued)

*Primary Examiner*—Cam N. Nguyen

(57) ABSTRACT

A process for preparing a catalyst by
(a) selecting a carrier which is a silica based carrier which has been subjected to a series of washings with one or more aqueous liquids consisting of aqueous liquids which have a pH of least 3, when measured at 20° C., or which is a silica based carrier which is formed from materials one or more of which have been subjected to this series of washings,
(b) precipitating a Group 8 metal compound onto the carrier,
(c) converting the precipitated Group 8 metal compound into metallic species, and
(d) subjecting the Group 8 metal/carrier composition to a purification treatment, before or after step (c); a catalyst which is obtainable by this process; and a process for preparing an alkenyl carboxylate by reacting a mixture comprising an olefin, a carboxylic acid and oxygen in the presence of the catalyst.

15 Claims, No Drawings

U.S. PATENT DOCUMENTS

| | | | |
|---|---|---|---|
| 6,207,610 B1 | 3/2001 | Krause et al. | |
| 6,303,536 B1 | 10/2001 | Chen et al. | 502/325 |
| 6,303,537 B1 | 10/2001 | Wang et al. | 502/330 |
| 6,391,821 B1 | 5/2002 | Satoh et al. | 502/300 |
| 6,420,308 B1 * | 7/2002 | Khanmamedova | 502/344 |
| 6,794,332 B2 * | 9/2004 | Khanmamedova et al. | 502/344 |
| 6,825,149 B2 * | 11/2004 | Khanmamedova | 502/330 |

FOREIGN PATENT DOCUMENTS

| | | |
|---|---|---|
| CN | 1068051 | 1/1993 |
| CN | 1250688 | 4/2000 |
| CN | 1268396 | 10/2000 |
| CN | 1297789 | 6/2001 |
| CN | 1297883 | 6/2001 |
| CN | 1340378 | 3/2002 |
| EP | 0519435 | 12/1992 |
| EP | 0634208 | 1/1995 |
| EP | 0634209 | 1/1995 |
| EP | 839793 | 5/1998 |
| EP | 0937498 | 8/1999 |
| EP | 965383 | 12/1999 |
| EP | 967009 | 12/1999 |
| EP | 976713 | 2/2000 |
| EP | 0985657 | 3/2000 |
| EP | 985657 | 3/2000 |
| EP | 1006100 | 6/2000 |
| EP | 1106247 | 6/2001 |
| EP | 909213 | 11/2001 |
| EP | 1175939 | 1/2002 |
| EP | 1205246 | 5/2002 |
| GB | 1283737 | 9/1968 |
| GB | 1215210 | 12/1970 |
| WO | 98/18553 | 5/1998 |
| WO | 99/08790 | 2/1999 |
| WO | 99/08791 | 2/1999 |
| WO | 99/42212 | 8/1999 |
| WO | 00/15333 | 3/2000 |
| WO | 00/15334 | 3/2000 |
| WO | 00/15335 | 3/2000 |
| WO | 00/58008 | 10/2000 |
| WO | 02/04392 | 1/2002 |

OTHER PUBLICATIONS

Periodic Table of the Elements as published in R C Weast (Ed,) "Handbook of Chemistry and Physics", 54$^{th}$ edition, CRC Press.

International Search Report dated Jul. 18, 2002.

S. Brunauer, P. Y. Emmett and E. Teller, J., "Adsorption of Gases in Multimolecular Layers", Am. Chem. Soc. vol. 60, 309-316, publ. Feb. 1938.

Periodic Table of the Elements as published in R C Weast (Ed,) "Handbook of Chemistry and Physics", 54$^{th}$ edition, CRC Press, Nov. 12, 1973.

* cited by examiner

US 7,425,647 B2

PROCESS FOR PREPARING A GROUP VIII-METAL CONTAINING CATALYST, USE THEREOF FOR PREPARING AN ALKENYL CARBOXYLATE

FIELD OF THE INVENTION

The invention relates to a process for preparing a catalyst, to a catalyst which is obtainable by the process of this invention, and to a process for preparing an alkenyl carboxylate comprising reacting a mixture comprising an olefin, a carboxylic acid and oxygen in the presence of the catalyst.

BACKGROUND OF THE INVENTION

Catalysts for the preparation of an alkenyl carboxylate from an olefin, a carboxylic acid and oxygen are known in the art. Such catalysts are based on a Group 8 metal as a catalytically active metallic species on a carrier. The preparation of the catalysts is well documented.

For example, the process for preparing the catalyst of U.S. Pat. No. 4,048,096 comprises the steps of selecting a carrier, precipitating a Group 8 metal compound into the carrier, converting the precipitated Group 8 metal compound into metallic species, and subsequently purifying the catalyst by washing with water.

Similar schemes for the preparation of the catalysts are known from U.S. Pat. Nos. 5,179,057 and 5,189,004. The latter documents highlight the removal from the catalysts of sodium ions, which are introduced during the catalyst preparation, for example as a portion of a precursor of the precipitated Group 8 metal compound (for example sodium tetrachloropalladium (II)), or as a portion of the precipitating agent which is used for precipitating the Group 8 metal compound (for example a sodium silicate or sodium hydroxide). Both documents teach that the removal of sodium ions leads to an increase in the activity of the catalyst and to a decrease in the selectivity when the catalyst is used in the process for the preparation of an alkenyl carboxylate.

U.S. Pat. Nos. 5,250,487 and 5,422,329 relate to Group 8 metal catalysts for use in a process for the preparation of an alkenyl carboxylate from an olefin, a carboxylic acid and oxygen. The catalysts are based on carrier particles which have been pressed with the aid of a binder of one or more salts of carboxylic acids. The carrier particles are washed with an acid for the removal of the cations of the binder from the support particles. The acid may be a mineral acid such as hydrochloric acid, sulfuric acid, phosphoric acid, or nitric acid. If the anion of the acid is detrimental to the catalyst, such as chloride and sulfate anions, excess acid may be removed by washing out with distilled water. If the salts employed during the subsequent catalyst preparation contain constituents harmful to the catalyst, such as chloride or sulfate, the catalyst is washed with water.

Thus, in the prior art documents relating to the Group 8 metal catalysts attention has been paid to the detrimental effects of certain catalyst impurities which are introduced intentionally during the carrier or catalyst preparation and to the removal of these impurities. Such impurities may be removed by using dedicated means. For example, the cations of the binder are removed by washing with acid.

WO-00/15333 teaches the preparation of improved catalysts, in particular silver impregnated alumina based catalysts for the vapor phase production of epoxides. The improvement is achieved by lowering the concentration of ionizable species present on the surface of the carrier, in particular by treating the carrier by washing with boiling water prior to catalyst preparation.

Although the known Group 8 metal catalyst have appreciable activity and selectivity in the preparation of alkenyl carboxylate from an olefin, a carboxylic acid and oxygen, further improvements of these catalysts are desirable, in particular in their ability to maintain their level of activity and selectivity during use over a long period of time.

SUMMARY OF THE INVENTION

It has now unexpectedly been found that the Group 8 metal catalysts having an improved catalyst performance in the preparation of alkenyl carboxylates are prepared if prior to the catalyst preparation the carrier is subjected to washing with water, even though water washing is also applied in the course of the catalyst preparation.

By the term "improved catalyst performance" it is meant that there is an improvement in at least one of the catalyst properties, which catalyst properties include catalyst activity, selectivity, activity or selectivity performance over time, operability (i.e. resistance to run-away), conversion and work rate. By "selectivity" it is meant the selectivity to alkenyl carboxylate, based on the quantity of olefin converted. The improvement in question concerns in particular the ability of the catalyst to maintain its level of activity and selectivity during use over a long period of time.

This result is unexpected in view of the prior teachings which relate to the Group 8 metal catalysts, as referred to hereinbefore. Namely, one skilled in the art would expect that the washings in the course of the catalyst preparation, as taught by these documents, would lead also to the removal of impurities already present in the carrier per se, so that no further advantageous effect could be expected from an additional washing of the carrier, i.e. prior to the catalyst preparation.

The beneficial effect of subjecting the carrier to washing with water, in addition to washing in the course of the catalyst preparation is also unexpected in view of WO-00/15333, referred to hereinbefore. Namely, WO-00/15333 does not teach any subsequent washing, i.e. as a step of the catalyst preparation or subsequent to the catalyst preparation.

Accordingly, the invention provides a process for preparing a catalyst which process comprises the steps of (a) selecting a carrier which is a silica based carrier which has been subjected to a series of washings with one or more aqueous liquids consisting of aqueous liquids which have a pH of least 3, when measured at 20° C., or which is a silica based carrier which is formed from materials one or more of which have been subjected to a said series of washings, (b) precipitating a Group 8 metal compound onto the carrier, (c) converting the precipitated Group 8 metal compound into metallic species, and (d) subjecting the Group 8 metal/carrier composition to a purification treatment, before or after step (c).

The invention also provides a process for preparing a catalyst which process comprises the steps of (a) washing a carrier with one or more aqueous liquids consisting of aqueous liquids which have a pH of least 3, when measured at 20° C., wherein the carrier is a silica based carrier, (b) precipitating a Group 8 metal compound onto the carrier, (c) converting the precipitated Group 8 metal compound into metallic species, and (d) subjecting the Group 8 metal/carrier composition to a purification treatment, before or after step (c).

The invention also provides a catalyst which is obtainable by a process for preparing a catalyst according to this invention.

The invention also provides a process for preparing an alkenyl carboxylate comprising reacting a mixture comprising an olefin, a carboxylic acid and oxygen in the presence of the catalyst of this invention.

DETAILED DESCRIPTION OF THE INVENTION

The silica based carrier for use in this invention may be of any kind. For example, the carrier may comprise further materials such as alumina, magnesia, zirconia, fuller's earth, artificial and natural zeolites, and combinations thereof, in particular alumina. The silica content of the carrier is typically at least 50% w, more typically at least 90% w, based on the weight of the carrier. Frequently the silica content of the carrier is at most 99.99% w, more frequently at most 99.9% w, on the same basis.

Typically, the carrier is a porous carrier, preferably having a specific surface area of at least 0.01 $m^2/g$, in particular in the range of from 0.05 to 1000 $m^2/g$, more in particular in the range of from 0.2 to 1000 $m^2/g$, as measured by the B.E.T. method, and a water absorption capacity of from 0.05 to 3 ml/g, in particular from 0.1 to 2 ml/g, as measured by conventional water absorption technique. The B.E.T. method as referred to herein has been described in detail in S. Brunauer, P. Y. Emmett and E. Teller, J. Am. Chem. Soc. 60, 309-16 (1938).

Of particular interest are silicas which have a specific surface area in the range of from 10 to 1000 $m^2/g$, in particular from 50 to 500 $m^2/g$, as measured by the B.E.T. method.

Regardless of the carrier used, it may be shaped into particles, chunks, pieces, and the like. Preferably, for use in a tubular fixed bed reactor, they are formed into a rounded shape, for example in the form of spheres, pellets, cylinders, rings or tablets, typically having dimensions in the range of from 2 mm to 2 cm.

For use in this invention, the carrier is subjected to a series of washings with one or more aqueous liquids. A series of washings is herein understood to include a single washing step and a combination of consecutive washing steps which employ one or more washing liquids. In accordance with this invention the washing liquids comprise aqueous liquids which all have a pH of at least 3, when measured at 20° C. One skilled in the art will appreciate that aqueous liquids may contain a small quantity of acid, such as resulting from dissolution of atmospheric carbon dioxide, and they may therefore have a pH slightly below 7, for example down to a pH of 3. Such aqueous liquids contain very little acid or the acid is a weak acid, so that yet they are considered to be essentially non-acidic aqueous liquids.

Preferably, the aqueous liquids have all a pH of at least 5, in particular at least 6, more in particular at least 7, when measured at 20° C. Typically, the washing liquids have all a pH of at most 10, in particular at most 9, more in particular at most 8, when measured at 20° C.

As used herein, the term "pH" refers to the pH of an aqueous liquid as measured by using a conventional pH measuring probe which is calibrated by using buffer solutions.

Eligibly, the aqueous liquids comprise for the greater part water, and they may or may not comprise relatively small quantities of other components, for example organic materials, for example esters, ethers, alcohols or ketones, or salts like acetates, carbonates, nitrates or oxalates, in particular such salts as lithium, sodium, potassium, ammonium, monoalkylammonium, dialkylammonium, trialkyl-ammonium and tetraalkylammonium salts. Such other components may not be detrimental to the preparation of the catalyst or to the performance of the catalyst when used in the preparation of alkenyl carboxylates. Otherwise, such other components, when left behind on the carrier after the washing may be removed from the carrier, for example by further washing the carrier, by evaporation or by decomposition (i.e. by calcination).

Not wishing to be bound by theory it is believed that as a result of the washing ionizable species are removed from the carrier, or at least from the carrier surface, which ionizable species have an influence on the precipitation and/or the conversion into metallic species, such that the morphology of the active surface of the catalyst is changed to an extent which favors the catalyst performance in the preparation of alkenyl carboxylates. It is believed that the following ionizable species may be associated with these effects: silicates, aluminosilicates, sulfates, chlorides, sodium salts, aluminium salts, calcium salts, magnesium salts, and the like.

The aqueous liquids which comprise a salt as specified hereinbefore may be called ion exchange solutions. The presence of salts in the aqueous liquids may facilitate the removal of ionizable species which are firmly bound to the carrier, so that a desirable result may be achieved in a shorter time or at a lower temperature.

Suitably, the ion exchange solution comprises the salt in a quantity of at most 0.1 moles/l. Suitably, the ion exchange solution comprises the salt in a quantity of at least 0.001 moles/l. Preferably, the ion exchange solution comprises the salt in a quantity in the range of from 0.002 to 0.05 moles/l. The remainder of the solution may be a de-ionized liquid as specified hereinafter.

The water content of the aqueous liquids, in particular when they do not comprise added salt as to form an ion exchange solution, is preferably at least 90% w, more preferably at least 99% w, in particular at least 99.9% w, more in particular at least 99.99% w, relative to the weight of the aqueous liquid. Frequently, the content of water is at most 99.999% w, on the same basis. Preferably, the aqueous liquid is water.

Suitably, the aqueous liquids have a low conductivity. Such low-conductivity aqueous liquids typically do not comprise added salt as to form an ion exchange solution. Suitably, the conductivity is at most 500 μmho (mho is $\Omega^{-1}$, or Siemen, or S), more suitably at most 100 μmho, preferably at most 20 μmho, in particular at most 5 μmho, when measured at 98° C. Frequently the conductivity will be at least 0.1 μmho, more frequently at least 0.2 μmho, on the same basis. Conductivities are herein understood to be electrical conductivities, measured by using a conductivity measuring probe having a cell constant of 1.0/cm. Suitably a YSI Model 3401 (trademark) conductivity measuring probe is used, connected to a YSI Model 35 (trade mark) conductance meter. Such low-conductivity aqueous liquids are typically de-ionized aqueous liquids. The de-ionized aqueous liquids are obtainable by de-ionisation using an ion exchange material such as an ion exchange resin, typically a cation exchange material in the acidic form, or an anion exchange material in the basis form, but preferably using a cation exchange material in the acidic ($H^+$) form and an anion exchange material in the basic ($OH^-$) form.

The extent and the type of washing are not material to the present invention. The washing may be carried out in a continuous fashion or it may be a batch type operation. There may be one washing, but the number of washings may also be two, or three, or more, for example up to five or ten. The quantity of aqueous liquid used in the washings relative to the quantity of the carrier is also not material to the invention. The washing may be carried out a temperature in the range of from 10 to 300° C., preferably at a temperature in the range of from 50 to 150° C., for example about 100° C. However, when using an ion exchange solution, the temperature is preferably in the range of from 20 to 120° C., for example about 70° C.

The washing may be monitored by applying a conductivity test, which conductivity test involves contacting samples of water with samples of the carrier, unwashed and washed, and measuring the conductivity of each water sample after it has reached equilibrium with the respective carrier sample at 95° C. In this conductivity test the conductivity is measured at 95° C., the quantity of water sample is 3 g/g carrier sample and the conductivity of the water prior to the contacting with the carrier sample is 1.5 µmho at 98° C. Water eligible for use in the conductivity test is water which is de-ionized using a cation exchange material in the H⁺ form and an anion exchange material in the OH⁻ form.

Typically the carrier is washed to the extent that in the conductivity test the conductivity measured for the washed carrier is less than 50% of the value found for the unwashed carrier, preferably less than 30%, more preferably less than 20%. Frequently, the carrier is washed to the extent that in the conductivity test the measured conductivity is at least 1%, more frequently at least 5% of the value found for the unwashed carrier.

Typically the carrier is washed to the extent that in the conductivity test the conductivity measured for the washed carrier is less than 200 µmho, more typically less than 75 µmho, preferably less than 50 µmho. The carrier may be washed such as to achieve that the conductivity measured in the conductivity test is as low as possible. However, in practice the carrier may be washed to the extent that the conductivity measured in the conductivity test is above 2 µmho, more frequently above 3 µmho.

As an alternative to, or in addition to washing the carrier, one or more materials from which the carrier is formed may be subjected to a series of washing as, and to the extent described hereinbefore. Subsequently, the carrier may be formed from the materials by conventional mixing and/or shaping methods, such as extrusion.

The Group 8 metal for use in this invention has suitably an atomic number of at least 44 and at most 78. One or more Group 8 metals may be applied. Preferably, the Group 8 metal is palladium.

Preferably, the catalyst is based on a Group 1b metal, in addition to a Group 8 metal. One or more Group 1b metals may be applied. The Group 1b metal is preferably gold.

The terms "Group 8 metal" and "Group 1b metal" as used herein refer to the metals of Group 8 and Group 1b, respectively, of the Periodic Table of the Elements as published in R C Weast (Ed,) "Handbook of Chemistry and Physics", 54$^{th}$ edition, CRC Press, inside cover.

In a preferred embodiment, the catalyst is based on palladium as the Group 8 metal and gold as the Group 1b metal.

The term "Group 8 metal/carrier composition", as used herein refers to any composition comprising the carrier and a Group 8 metal dispersed on the carrier, irrespective of whether the Group 8 metal is present as a Group 8 metal compound or Group 8 metal compound precursor, or in the form of metallic species.

Suitably the Group 8 metal compound and optionally the Group 1b metal compound is precipitated onto the carrier by pore impregnating the carrier with one or more aqueous solutions comprising a Group 8 metal compound precursor and optionally a Group 1b metal compound precursor and then precipitating the Group 8 metal compound and optionally the Group 1b metal compound onto the carrier from such solutions, by using a precipitating agent. In more detail, the applicable materials and methods may be those as disclosed in U.S. Pat. Nos. 4,048,096, 5,179,057 and 5,189,004, which are incorporated herein by reference.

The volume of an impregnation solution preferably corresponds to at least 80%, preferably 95 to 100% of the water absorption capacity of the carrier.

Eligible Group 8 metal compound precursors and Group 1b metal compound precursors are for example water soluble acids and salts, such as chlorides, nitrates, nitrites and sulfates. Preferred such Group 8 containing acids and salts are palladium (II) chloride, palladium (II) nitrate, and palladium (II) sulfate and, in particular, sodium palladium (II) tetrachloride. Preferred such Group 1b metal containing acids and salts are auric (III) chloride and, in particular, tetrachloroauric (III) acid.

The precipitating agent includes for example alkali metal hydroxides, alkali metal bicarbonates, alkali metal carbonates and, preferably, alkali metal silicates. Suitable alkali metals are lithium, sodium and potassium. The preferred precipitating agent is sodium silicate. A useful form of sodium silicate is sodium metasilicate pentahydrate. The precipitating agent is suitably used in an excess relative to the Group 8 metal and optionally the Group 1b metal, taken together. For example, the precipitating agent may be used in a quantity of 1 to 3 moles, preferably 1.5 to 2.5 moles per mole of Group 8 metal compound precursor. If the Group 1b metal precursor is present an additional quantity of the precipitating agent may be used, for example 2 to 10 moles, preferably 2.5 to 8 moles per mole of Group 1b metal compound precursor.

The precipitating agent is preferably used as an aqueous solution. The aqueous solution has typically a volume sufficient to cover the impregnated, wet carrier particles. As an alternative, after the impregnation with one or more solutions comprising a Group 8 metal compound precursor and optionally a Group 1b metal compound precursor, the carrier particles may be dried and subsequently impregnated with an aqueous solution comprising the precipitating agent. In the latter case, the volume of the aqueous solution of the precipitating agent typically corresponds to at least 80%, preferably 95 to 100% of the water absorption capacity of the carrier.

The temperature at which the precipitation may be carried out is typically in the range of from 1 to 100° C., more typically in the range of from 5 to 50° C., for example about 20° C. The reaction time applied in the precipitation step may be for example at least 2 hours, more preferably at least 3 hours, and it may be for example up to 100 hours, more typically it is in the range of from 6 to 40 hours, for example 24 hours. During the precipitation, the particles may be left static, or they may be moved relative to the solution of the precipitation agent, or relative to each other. For example, the particles may be moved relatively to each other during the initial stages of the precipitation, for example during the first 15 minutes, or first 30 minutes, or first hour. Upon completion of the precipitation, the pH of the precipitating solution is preferably in the range of from 6.5 to 11, for example 6.5 to 9.5, but more preferably it is in the range of from 7.5 to 10, in particular from 7.5 to 8, when measured at 20° C. The final pH may be adjusted by changing the amount of the precipitating agent.

The quantity of the Group 8 metal compound precursor may be such that in the catalyst as prepared the content of the Group 8 metal is typically in the range of from 10 to 500 mmoles/kg catalyst, and preferably in the range of from 20 to 200 mmoles/kg catalyst, for example about 75 mmoles/kg or about 138 mmoles/kg.

The quantity of the Group 1b metal compound precursor may be such that in the catalyst as prepared the content of the Group 1b metal is typically in the range of from 1 to 200 mmoles/kg catalyst, and preferably in the range of from 5 to 100 mmoles/kg catalyst, for example about 37.2 mmoles/kg or about 65 mmoles/kg.

The precipitated Group 8 metal compound and, if present, the Group 1b metal compound may be converted into metallic species. If the Group 8 metal in the Group 8 metal compound and, if present, the Group 1b metal in the Group 1b metal compound are not in their zero valence state, the conversion into metallic species may be accomplished by reduction. Suitable reducing agent and reduction methods are known from U.S. Pat. Nos. 4,048,096, 5,179,057 and 5,189,004, which are incorporated herein by reference.

For example, the reduction may be accomplished by using as a reducing agent diborane; amines, such as ammonia and hydrazine; carboxylic acids and their salts, such as oxalic acid, potassium oxalate, formic acid, potassium formate, ammonium citrate; aldehydes, such as formaldehyde, acetaldehyde; hydrogen peroxide; reducing sugars such as glucose; alcohols other than reducing sugars, such as methanol and ethanol; polyhydric phenols, such as hydroquinone and catechol; hydrogen; carbon monoxide; olefins, such as ethylene, propene and isobutene; or sodium borohydride. The reduction may be carried out in an aqueous solution which comprises for example at most 50 mole, preferably at most 25 mole of the reducing agent per mole of Group 8 metal present in the Group 8 metal compound and, if present, the Group 1b metal in the Group 1b metal compound. This will frequently result in a complete reduction of the Group 8 metal and, if present, the Group 1b metal. Suitably, so much of the reducing agent is used which is sufficient to complete the reduction of at least 90%, more suitably at least 99% of the Group 8 metal and, if present, the Group 1b metal to metallic species.

Preferably, hydrogen is employed as the reducing agent. When hydrogen is employed, typically no liquid diluent is present, typically the absolute pressure is in the range of from 50 to 2000 kPa (0.5 to 20 bar), more typically from 100 to 1000 kPa (1 to 10 bar), typically the hydrogen partial pressure is in the range of from 1 to 2000 kPa (0.01 to 20 bar), and typically the temperature is in the range of from 10 to 300° C., more typically from 50 to 250° C.

In another preferred embodiment, hydrazine is employed as the reducing agent. When hydrazine is employed, typically an aqueous diluent is present, and typically the temperature is in the range of from 0 to 100° C., more typically from 5 to 50° C., for example 20° C.

Combinations of reducing agents may be used, or two or more separate reduction steps may be applied. For example, the precipitated Group 8 metal compound and, if present, the precipitated Group 1b metal compound may be reduced in part with a first reducing agent, for example about 20%-mole or about 40%-mole or about 60%-mole of the total of Group 8 metal and Group 1b metal (if any), and in a subsequent step, the remaining part may be reduced with a second reducing agent. The first and second reducing agents may independently be selected from the reducing agents described hereinbefore.

Preferred first reducing agents are selected from diborane; amines, such as ammonia and hydrazine; carboxylic acids and their salts, such as oxalic acid, potassium oxalate, formic acid, potassium formate, ammonium citrate; aldehydes, such as formaldehyde, acetaldehyde; hydrogen peroxide; reducing sugars such as glucose; polyhydric phenols, such as hydroquinone and catechol; or sodium borohydride. The preferred first reducing agent is hydrazine.

The second reducing agents may suitably be selected from hydrogen; carbon monoxide; alcohols, such as methanol and ethanol; aldehydes, such as formaldehyde and acetaldehyde; and olefins, such as ethylene, propene and isobutene. The preferred second reducing agent is hydrogen.

The reduction in which the first reducing agent is employed is preferably carried out as a liquid phase reaction, i.e. a reduction which involves contacting the Group 8 metal/carrier composition with the first reducing agent present in a liquid phase. The reduction in which the second reducing agent is employed is preferably carried out as a gas phase reaction, i.e. a reduction which involves contacting the Group 8 metal/carrier composition with the second reducing agent present in a gas phase, in the absence of a continuous liquid phase, preferably in the absence of a liquid phase.

In a particular embodiment, a major amount of the precipitated Group 8 metal compound and, if present, the precipitated Group 1b metal compound may be reduced in the liquid phase reaction by using the first reducing agent. This may be achieved by employing a suitable amount of the first reducing agent and allowing the first reducing agent to completely react away. More of the first reducing agent may be needed if it has a tendency to decompose, under the prevailing reaction conditions. The major amount may be at least 50%-mole, and preferably it may represent from 70 to 99%-mole, more preferably from 80 to 90%-mole, of the total of the Group 8 metal and Group 1b metal (if any). In this particular embodiment, the reduction with the first reducing agent may be followed by the purification step (c), subsequently optionally by a drying step as described hereinafter, and thereafter the remaining part of the Group 8 metal and Group 1b metal (if any) may be reduced with the second reducing agent, in particular, hydrogen. This sequence of steps is advantageous as problems are avoided which are associated with the disposal of excess, unconverted reducing agents (these may be noxious materials, such as hydrazine), while it minimizes possible losses of Group 8 metal and Group 1b metal (if present) during the purification step (c), and it leads to a high yield of metallic species on the catalyst. Further, it has unexpectedly been found that by applying the combination of a liquid phase reaction and a gas phase reaction instead of applying the liquid phase reaction only, there is an improvement in the dispersity of the metallic species in the catalyst, as measured by an increased carbon monoxide chemisorption of the catalyst. It is theorized that a better dispersity of the metallic species leads to an improved catalyst performance.

In another embodiment the Group 8 metal compound precursor and, if present, optionally the Group 1b metal compound precursor is precipitated and converted into metallic species in one step, following for example procedures as disclosed in WO-99/08790 and WO-99/08791. This means that in the catalyst preparation according to this invention step (b) and step (c) may be carried out as a single step.

The purification treatment suitably involves a series of washings of the Group 8 metal/carrier composition, with one or more aqueous liquids, with the objective of removing at least a portion of the useless chemicals, which are left on the Group 8 metal/carrier composition after accomplishing the precipitation of the Group 8 metal compound on the carrier, and, optionally, after converting the Group 8 metal compound into metallic species.

Eligibly, the aqueous liquids for use in the purification treatment may be selected from the aqueous liquids as specified hereinbefore for the washing of the carrier of steps (a).

The purification treatment may be carried out at a temperature in the range of from 0 to 100° C., preferably at a temperature in the range of from 5 to 50° C., for example about 20° C.

The purification treatment may be monitored by any suitable means, for example by applying the conductivity test as described hereinbefore. Alternatively, the purification treatment may be monitored by following the disappearance of contaminants which are to be removed, such as sodium ions or chloride, in accordance with the nature of, for example, the Group 8 metal compound precursor, the precipitating agent and the reducing agent. In this respect, reference may be made to U.S. Pat. Nos. 4,048,096, 5,179,057 and 5,189,004, which are incorporated herein by reference.

The purification treatment, i.e. step (d), may be carried out after step (c) and before an optional step (e), as described hereinafter, or after step (b) and before step (c). As set out hereinbefore, it may be advantageous to carry out a step (c) before step (d) and to carry out another step (c) after step (d), and suitably before an optional step (e).

The present process for preparing a catalyst may comprise in addition the step of (e) impregnating with a source of an alkali metal, such as disclosed in U.S. Pat. Nos. 4,048,096, 5,179,057 and 5,189,004, which are herein incorporated by reference. Any source of an alkali metal may be used such that the alkali metal deposited on the Group 8 metal/carrier composition can form an alkali metal carboxylate or maintain the presence of an alkali metal carboxylate upon contact with an carboxylic acid, such as during the subsequent use of the catalyst in the preparation of an alkenyl carboxylate.

Suitable sources of an alkali metal are for example alkali metal carbonates and, preferably, alkali metal carboxylates. The alkali metal carboxylate is typically derived from a mono carboxylic acid, such as butyric acid, propionic acid and, preferably, acetic acid. The alkali metal may be any one or more of lithium, sodium, potassium, rubidium and cesium. Preferably, the alkali metal is potassium. The preferred alkali metal carboxylate is potassium acetate. The quantity of the alkali metal carboxylate is typically such that the alkali metal content of the catalyst is in the range of from 0.1 to 5 mole/kg, more preferably from 0.2 to 2 mole/kg catalyst, for example 340 mmole/kg, or 585 mmole/kg, or 765 mmole/kg, or 1560 mmole/kg.

The step of impregnating with an alkali metal carboxylate may be carried out at any stage of the catalyst preparation. Preferably, the Group 8 metal/carrier composition is impregnating with an alkali metal carboxylate after step (d), in particular after step (d) and step (c).

At certain stages of the catalyst preparation it may be desirable to perform a drying step. Drying is typically performed at a temperature in the range of from 50 to 300° C., more typically in the range of from 80 to 150° C., for example 90° C., or 115° C., or 120° C., using an inert gas, such as nitrogen or helium, or air.

A drying step may be carried out, for example, following the initial carrier washing (cf. steps (a)), following the purification treatment (cf. step (d)) or following the impregnation of step (e). Preferably, the last step in the catalyst preparation in which liquids are involved is a drying step, after which the catalyst may or may not be subjected to essentially dry operations, such as milling and sieving.

The catalyst which is prepared by the methods described hereinbefore is typically a shell type catalyst, i.e. a catalyst which comprises the catalytically active species, i.e. the Group 8 metallic species, in the surface layer of the carrier. For example, 90 mole-% of the Group 8 metallic species may be distributed within the surface layer extending at most 2 mm from the surface of the carrier. In more preferred embodiments, 90 mole-% of the Group 8 metallic species may be distributed within the surface layer extending at most 1.5 mm, in particular at most 1 mm, from the surface of the carrier. Frequently the surface layer in question extends at least 0.05 mm, in particular at least 0.1 mm, from the surface of the carrier.

The present process for preparing an alkenyl carboxylate comprises reacting a mixture comprising an olefin, a carboxylic acid and oxygen in the presence of the catalyst of this invention. The process is frequently a gas phase process, wherein a gaseous feed comprising the reactants is contacted with the solid catalyst. The catalyst is suitably present in the form of a fluidized bed of catalyst particles, or, more suitable, in the form of a packed bed. The process may be carried out as a batch process, however, it is more suitable to carry out the process as a continuous process.

The carboxylic acid is preferably a monocarboxylic acid, for example butyric acid, propionic acid, or preferably acetic acid.

The olefin is typically a monoolefin, for example 1-butene, 2-butene, isobutene, propylene, or preferably ethylene.

Most preferably, the carboxylic acid is acetic acid and the olefin is ethylene, in which case the alkenyl carboxylate is vinyl acetate.

The quantity of carboxylic acid is suitably in the range of from 1 to 20%-mole, more suitably in the range of from 5 to 15%-mole, relative to the number of moles of the feed. The quantity of olefin is suitably in the range of from 10 to 80%-mole, more suitably in the range of from 30 to 60%-mole, relative to the number of moles of the feed. The quantity of oxygen is suitably in the range of from 1 to 15%-mole, more suitably in the range of from 5 to 10%-mole, relative to the number of moles of the feed. One skilled in the art will understand that for a gaseous feed a mole fraction corresponds with a volume fraction.

The source of oxygen may be air. Air may be used in the process of this invention, but it is preferred that an oxygen containing gas which may be obtained by separation from air is used.

Furthermore, inert compounds may be present in the mixture, for example methane, ethane, carbon dioxide, nitrogen or argon. Inert compounds may typically be present in a quantity of from 5 to 80%-mole, more typically from 10 to 60%-mole, relative to the number of moles of the feed.

The process may preferably be carried out at a temperature in the range of from 100 to 250° C., in particular in the range of from 130 to 200° C. As time proceeds, the temperature may be increased gradually, as to compensate for loss in activity of the catalyst, if any. The process may preferably be carried out at a pressure in the range of from 1 to 25 barg (i.e. bar gauge), in particular in the range of from 1 to 20 barg.

In general, it is preferred to operate at a high oxygen concentration. However, in actual practice in order to remain outside the flammability limits of the reactor streams, the concentration of oxygen has to be lowered as the concentration of the olefin and/or oxygenate is increased. The actual safe operating conditions depend along with the gas composition, also on individual plant conditions, such as temperature and pressure. Therefore, for each individual plant the concentration of oxygen will be determined which may be used with any concentration of the olefin and the oxygenate.

When operating the process as a gas phase process using a packed bed reactor, the GHSV may preferably be in the range of from 1000 to 10000 Nl/(l.h). The term "GHSV" stands for the Gas Hourly Space Velocity, which is the volumetric flow rate of the feed, which is herein defined at normal conditions (i.e. 0° C. and 100 kPa (1 bar) absolute), divided by the volume of the catalyst bed.

The alkenyl carboxylate may be recovered from the reaction product by known means, such as by fractional distillation or reactive distillation.

Unless specified otherwise, the organic compounds mentioned herein have typically at most 10 carbon atoms, in particular at most 6 carbon atoms. Organic compounds are deemed to be compounds which comprise carbon atoms and hydrogen atoms and carbon-hydrogen bonds in their molecules.

It is apparent that certain features of the invention, which are for clarity described herein in the context of separate embodiments, may also be provided in combination in a single embodiment. Conversely, features of the invention which are described in the context of a single embodiment may also be provided separately or in any suitable sub-combination.

The invention will be illustrated by means of the following, non-limiting examples.

EXAMPLE 1

For Comparison

A catalyst was prepared by applying the following steps:

1. A 25 g sample of a silica spheres carrier (spheres diameter 5 mm, surface area 137 m$^2$/g, water absorption capacity 0.63 ml/g, obtained from Südchemie, under the trademark KA-160), was dried at 120° C. in air, cooled down to ambient temperature in a dessicator and subsequently impregnated with 15.7 ml of a solution of sodium palladium (II) tetrachloride (III) (Na$_2$PdCl$_4$) and tetrachloroauric acid (HAuCl$_4$) in de-ionized water containing 0.220 g palladium and 0.121 g gold. A container holding the carrier was gently shaken to allow solution uptake by the carrier. After complete uptake of the solution the impregnated carrier was allowed to stand for 2 hours at room temperature.

2. Then 30 ml of a solution containing 1.68 g sodium metasilicate pentahydrate (Na$_2$SiO$_3$.5H$_2$O) was added to completely cover the wet impregnated support. This was allowed to stand for 15 hours.

3. Subsequently, 1 ml of 85% w hydrazine hydrate was added, mixed gently and allowed to stand for 4 hours at room temperature to reduce the palladium and gold salts to metallic species.

4. The palladium/carrier composition was then washed with distilled de-ionized water three times by decantation followed by a continuous wash until the wash water was free of chloride, as checked by the absence of a precipitate when tested with a silver nitrate solution. The washed palladium/carrier composition was then dried at about 120° C. for 4 hours under nitrogen, and cooled in a container protected from moisture 5. The palladium/carrier composition was then impregnated with 15.7 ml of a solution of potassium acetate in de-ionized water containing 1.34 g potassium, dried at about 120° C. for 15 hours under nitrogen, and cooled.

The catalyst thus prepared was tested in a reaction tube having a length of 30 cm and an inside diameter of 1.51 cm. The tube was loaded with 2.5 g of catalyst diluted into a 10 cm bed of glass beads. The reaction tube was fed with a gaseous mixture of 49 mole-% ethylene, 13 mole-% acetic acid and 7.6 mole-% oxygen (balance nitrogen). The GHSV was 4250 Nl/(l.h), calculated on undiluted catalyst. With the catalyst temperature initially at 147° C., and the absolute pressure at 880 kPa (i.e. 7.8 barg), the space-time-yield was 750 g vinyl acetate/(l catalyst.h), and the initial selectivity was 93%. The jacket temperature was increased slowly so as to keep the space-time-yield constant at 750 g vinyl acetate/(l catalyst.h). After 425 hours, the jacket temperature was 190° C., and the selectivity was 84%.

EXAMPLE 2

According to the Invention

The procedures of Example 1 was repeated, except that the sample of silica spheres carrier was subjected to washing before use in step 1. This washing was carried out by immersing a 500 g sample of the carrier in boiling de-ionized water (6 kg, having a conductivity of 1.5 μmho at 98° C.) in a continuously replenishing vessel (flow rate 0.76 l/min). The conductivity of the washing water was measured continuously at 95° C. After 12 minutes the peak value of the conductivity was 60 μmho and after 120 minutes the conductivity was 6 μmho, at which point the carrier was subjected to the drying of step 1.

At any point in time the washing water may be deemed to have reached equilibrium with the carrier. The conductivity data so obtained represent fairly the values which would be obtained when applying the conductivity test, as described hereinbefore, to the unwashed carrier and the washed carrier, respectively.

In testing the catalyst, the space-time-yield was kept constant at 750 g vinyl acetate/(l catalyst.h) by increasing the jacket temperature. The initial selectivity was 93%, and after 425 hours, the jacket temperature was 168° C., and the selectivity was 91%.

EXAMPLE 3

According to the Invention, Prophetic

A catalyst is prepared in accordance with the procedures of Example 2, except for the following differences: step 3 is omitted, and following step 4 the palladium/carrier composition is dried in air at 120° C., then subjected to reduction in a hydrogen/nitrogen (20:80 v/v) mixture, at a flow rate of the hydrogen/nitrogen mixture of 500 Nl/(l catalyst.h), at a temperature of 200° C., and at an absolute pressure of 110 kPa (1.1 bar), during 4 hours.

EXAMPLE 4

According to the Invention, Prophetic

A catalyst is prepared in accordance with the procedures of Example 2, except for the difference that step 3 is omitted, and that instead the palladium/carrier composition is dried in air at about 120° C., and cooled, and then subjected to reduction in a hydrogen/nitrogen (20:80 v/v) mixture, at a flow rate of the hydrogen/nitrogen mixture of 500 Nl/l(l catalyst.h), at a temperature of 200° C., and at an absolute pressure of 110 kPa (1.1 bara), during 4 hours.

EXAMPLE 5

A catalyst was prepared from washed and dried carrier as obtained in Example 2, by applying the following steps:

1. A 25 g sample of the washed and dried carrier was impregnated with 15.7 ml of a solution of sodium palladium (II) tetrachloride (III) (Na$_2$PdCl$_4$) and tetrachloroauric acid (HAuCl$_4$) in de-ionized water containing 0.220 g palladium and 0.121 g gold. A container holding the carrier was gently shaken to allow solution uptake by the carrier. After complete uptake of the solution the impregnated carrier was allowed to stand for 2 hours at room temperature.

2. Then 30 ml of a solution containing 1.68 g sodium metasilicate pentahydrate (Na$_2$SiO$_3$.5H$_2$O) was added to completely cover the wet impregnated support. This was allowed to stand for 15 hours.

3. Subsequently, 2.5 ml. of 2.8% w hydrazine hydrate in water was added, mixed gently and allowed to stand for 4 hours at room temperature. This led to the reduction of about 55 mole-% of the total of the palladium and gold salts to metallic species.

4. The palladium/carrier composition was then washed with distilled de-ionized water three times by decantation followed by a continuous wash until the wash water was free of chloride, as checked by the absence of a precipitate when tested with a silver nitrate solution. The washed palladium/carrier composition was then dried at about 120° C. for 4 hours under nitrogen, and cooled in a container protected from moisture.

5. The palladium/carrier composition was then subjected to reduction in a hydrogen/nitrogen (15:85 v/v) mixture, at a flow rate of the hydrogen/nitrogen mixture of 500 Nl/(l catalyst.h), at a temperature of 220° C., and at a pressure of 100 kPa, until completion of the reduction, i.e. about 2 hours.

6. The palladium/carrier composition was then impregnated with 15.7 ml of a solution of potassium acetate in de-ionized water containing 1.34 g potassium, dried at about 120° C. for 15 hours under nitrogen, and cooled.

The catalyst thus prepared had a palladium content of 0.75% w, a gold content of 0.4% w and its carbon monoxide chemisorption was 25.3 mmol per kg catalyst.

EXAMPLE 6

Prophetic

Vinyl acetate is prepared as follows.

The catalyst prepared in Example 5 is tested in a reaction tube having a length of 30 cm and an inside diameter of 1.51 cm. The tube is loaded with 2.5 g of catalyst diluted into a 10 cm bed of glass beads. The reaction tube is fed with a gaseous mixture of 49 mole-% ethylene, 13 mole-% acetic acid and 7.6 mole-% oxygen (balance nitrogen). The GHSV is 4250 Nl/(l.h), calculated on undiluted catalyst, and the pressure is 880 kPa (i.e. 7.8 barg). With the catalyst temperature initially at 147° C., vinyl acetate is produced. The jacket temperature is increased slowly so as to keep the space-time-yield constant.

EXAMPLE 7

Prophetic

Example 5 is repeated, with the exception that, in step 3, 2.5 ml of 12% w hydrazine hydrate in water is used instead of 2.5 ml of 2.8% w hydrazine hydrate in water. This leads in this step 3 to the reduction of about 82-85 mole-% of the total of the palladium and gold salts to metallic species.

The catalyst so prepared is tested in the preparation of vinyl acetate as described in Example 6.

We claim:

1. A process for preparing a catalyst which process comprises the steps of (a) precipitating a Group 8 metal compound onto a silica based carrier which has been subjected to a series of washings with one or more aqueous liquids consisting of aqueous liquids which have a pH of at least 3, when measured at 20° C., or a silica based carrier which is formed from materials one or more of which have been subjected to said series of washings;

(b) converting the precipitated Group 8 metal compound into metallic species; and (c) subjecting the Group 8 metal/carrier composition resulting from step (a) or step (b) to a purification treatment.

2. The process as claimed in claim 1, wherein the washing liquid is water.

3. The process as claimed in claim 1, wherein the extent of washing is such that in a conductivity test the conductivity measured for the washed carrier is less than 30% of the value found for the unwashed carrier, wherein the conductivity test comprises contacting samples of water with samples of the unwashed carrier and the washed carrier and measuring at 95° C. the conductivity of each water sample after it has reached equilibrium with the respective carrier sample at 95° C., the quantity of water sample being 3 g/g carrier sample, the conductivity of the water prior to the contacting with a carrier sample being 1.5 µmho at 98° C., and the conductivities being measured by using a conductivity measuring probe having a cell constant of 1.0/cm.

4. The process as claimed in claim 3, wherein the extent of washing is such that in the conductivity test the conductivity measured for the washed carrier is less than 20% of the value found for the unwashed carrier.

5. The process as claimed in claim 1, wherein the extent of washing is such that in a conductivity test the conductivity measured for the washed carrier is less than 75 µmho, wherein the conductivity test comprises contacting a sample of water with a sample of the washed carrier and measuring at 95° C. the conductivity of the water sample after it has reached equilibrium with the carrier sample at 95° C., the quantity of water sample being 3 g/g carrier sample, the conductivity of the water prior to the contacting with the carrier sample being 1.5 µmho at 98° C., and the conductivities being measured using a conductivity measuring probe having a cell constant of 1.0/cm.

6. The process as claimed in claim 5, wherein the extent of washing is such that in the conductivity test the conductivity measured for the washed carrier is less than 50 µmho.

7. The process as claimed in claim 1, wherein the Group 8 metal and optionally in addition a Group 1b metal is precipitated onto the carrier by pore impregnating the carrier with one or more aqueous solutions comprising a Group 8 metal compound precursor and optionally a Group 1b metal compound precursor and then precipitating a Group 8 metal compound and optionally a Group 1b metal compound onto the carrier from such solutions, by using a precipitating agent.

8. The process as claimed in claim 7, wherein the Group 8 metal compound precursors and the optional Group 1b metal compound precursors are selected from water soluble acids and salts of palladium and optionally gold and the precipitating agent is selected from the group consisting of hydroxides, bicarbonates, carbonates and silicates of lithium, sodium and potassium.

9. The process as claimed in claim 1, wherein the precipitated Group 8 metal compound and, if present, a precipitated Group 1b metal compound is converted into metallic species by reduction employing hydrogen as the reducing agent.

10. The process as claimed in claim 1, wherein the purification treatment involves a series of washings with one or more aqueous liquids.

11. The process as claimed in claim 1, which comprises in addition a step of (d) impregnating the purified Group 8 metal/carrier composition with a source of an alkali metal.

12. A catalyst prepared by a process comprising the steps of
   (a) precipitating a Group 8 metal compound onto a silica based carrier which has been subjected to a series of washings with one or more aqueous liquids consisting of aqueous liquids which have a pH of least 3, when measured at 20° C., or a silica based carrier which is formed from materials one or more of which have been subjected to said series of washings;
   (b) converting the precipitated Group 8 metal compound into metallic species; and
   (c) subjecting the Group 8 metal/carrier composition resulting from step (a) or step (b) to a purification treatment.

13. The catalyst as claimed in claim 12, which comprises palladium as the Group 8 metal in a quantity in the range of from 10 mmoles/kg to 500 mmoles/kg catalyst, and in addition gold as a Group 1b metal in a quantity in the range of from 1 mmoles/kg to 200 mmoles/kg catalyst, and an alkali metal in a quantity in the range of from 0.1 mmoles/kg to 5 mole/kg catalyst.

14. A process for preparing an alkenyl carboxylate comprising reacting a mixture comprising an olefin, a carboxylic acid and oxygen in the presence of a catalyst prepared by a process comprising the steps of
   (a) precipitating a Group 8 metal compound onto a silica based carrier which has been subjected to a series of washings with one or more aqueous liquids consisting of aqueous liquids which have a pH of least 3, when measured at 20° C., or a silica based carrier which is formed from materials one or more of which have been subjected to said series of washings;
   (b) converting the precipitated Group 8 metal compound into metallic species; and
   (c) subjecting the Group 8 metal/carrier composition resulting from step (a) or step (b) to a purification treatment.

15. The process as claimed in claim 14, wherein the catalyst comprises palladium as the Group 8 metal in a quantity in the range of from 10 mmoles/kg to 500 mmoles/kg catalyst, and in addition gold as a Group 1b metal in a quantity in the range of from 1 mmoles/kg to 200 mmoles/kg catalyst, and an alkali metal in a quantity in the range of from 0.1 mmoles/kg to 5 mole/kg catalyst.

* * * * *